United States Patent [19]

Effenberger et al.

[11] Patent Number: 4,523,012

[45] Date of Patent: Jun. 11, 1985

[54] S-SUBSTITUTED 2-AZIDO-3-MERCAPTO-PROPIONIC ACID ESTER AND PROCESS FOR ITS PRODUCTION AND USE

[75] Inventors: Franz Effenberger; Thomas Beisswenger, both of Stuttgart, Fed. Rep. of Germany

[73] Assignee: Degussa Aktiengesellschaft, Frankfurt am Main, Fed. Rep. of Germany

[21] Appl. No.: 457,391

[22] Filed: Jan. 12, 1983

Related U.S. Application Data

[63] Continuation-in-part of Ser. No. 418,843, Sep. 16, 1982, Pat. No. 4,456,766.

[30] Foreign Application Priority Data

Jan. 15, 1982 [DE] Fed. Rep. of Germany ....... 3200994

[51] Int. Cl.³ .......................................... C07C 149/243
[52] U.S. Cl. .................................. 544/316; 260/349; 562/557
[58] Field of Search ................. 260/140, 349; 544/316

[56] References Cited

FOREIGN PATENT DOCUMENTS 3140227 12/1982 Fed. Rep. of Germany .

OTHER PUBLICATIONS

Kakimoto, Chemistry Letters, 527 (1982).

Primary Examiner—Robert Gerstl
Attorney, Agent, or Firm—Cushman, Darby & Cushman

[57] ABSTRACT

The subject matter of the invention are S-substituted 2-azido-3-mercapto-propionic acid esters of the general formula

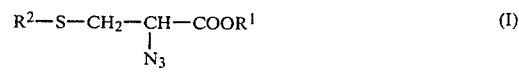

in which $R^1$ is a methyl or ethyl group and $R^2$ is an unsubstituted or substituted alkyl group, a cycloalkyl group, an unsubstituted or substituted aromatic or heteroaromatic group or a benzyl group, and a process for their production by reaction of a methyl or ethyl ester of 2-chloroacrylic acid with a corresponding thiol to form an S-substituted 2-chloro-3-mercapto-propionic acid ester and subsequently exchanging the chlorine atom with an azido group as well as use of the compounds of formula (I) as intermediate products in the production of D,L-cysteine or derivatives of D,L-cysteine.

9 Claims, No Drawings

S-SUBSTITUTED 2-AZIDO-3-MERCAPTO-PROPIONIC ACID ESTER AND PROCESS FOR ITS PRODUCTION AND USE

CROSS-REFERENCE TO RELATED APPLICATION

This application is a continuation-in-part of application Ser. No. 418,843 filed Sept. 16, 1982, now U.S. Pat. No. 4,456,766.

BACKGROUND OF THE INVENTION

The subject matter of the invention are S-substituted 2-azido-3-mercapto-propionic acid esters of the general formula:

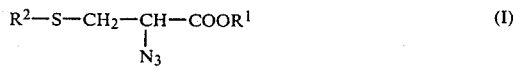

in which $R^1$ is a methyl or ethyl group and $R^2$ is an unsubstituted or substituted alkyl group, a cycloalkyl group, an unsubstituted or substituted aromatic or heteroaromatic group or a benzyl group, and a process for their production by reaction of a methyl or ethyl ester of 2-chloroarcyclic acid of the general formula:

where $R^1$ is a methyl or ethyl group with a thiol of the general formula:

in which $R^2$ is as defined above to form an S-substituted 2-chloro-3-mercapto-propionic acid ester of the general formula:

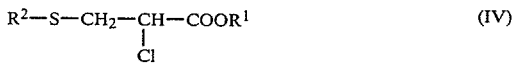

in which $R^1$ and $R^2$ are as defined above and subsequently exchanging the chlorine atom with an azido group by means of an alkali metal azide (e.g. sodium azide or potassium azide) in the presence of a phase transfer catalyst.

The compounds of general formula (I) are valuable intermediate products for the production of D,L-cysteine and S-substituted derivatives of D,L-cysteine.

Therefore, a further purpose of the invention is the use of S-substituted 2-azido-3-mercapto-propionic acid esters of general formula (I) as intermediate products in the production of D,L-cysteine or derivatives of D,L-cysteine.

The process for the production of the compounds of general formula (I) according to the invention starts from the readily accessible methyl or ethyl ester of the 2-chloroacrylic acid and in both reaction steps proceeds with high yields.

In the first reaction step the methyl or ethyl ester of 2-chloroacrylic acid is reacted with a thiol of general formula (III) to form an S-substituted 2-chloro-3-mercapto-propionic acid ester of general formula IV. Suitable thiols for example, are methyl mercaptan, ethyl mercaptan, n-propyl mercaptan, n-butyl mercaptan, n-pentyl mercaptan, n-hexyl mercaptan, isopropyl mercaptan, isobutyl mercaptan, secondary butyl mercaptan, n-octyl mercaptan, cyclopentyl mercaptan, cyclohexyl mercaptan, thioglycolic acid methyl ester thioglycolic acid ethyl ester, thioglycolic acid benzyl ester, thioglycolic acid octyl ester, 3-mercaptopropionic acid ethyl ester, thiophenol, 2-chlorothiophenyl, 3-chlorothiophenol, 4-chlorothiophenol, 2,4-dichlorothiophenol, 3,4-dichlorothiophenol, 3,5-dichlorothiophenol, 2-methylthiophenol, 4-methylthiophenol, 3,5-dimethoxythiophenol, 2-fluorothiophenol, 4-fluorothiophenol, 3-trifluoromethylthiophenol, 4-cyanothiophenol, 4-nitrothiophenol, 3-methylmercaptothiophenol, 2-mercaptopyrimidine, bis-(dimethylamino)-mercapto-s-triazine, bis-(dimethoxy)-mercapto-s-triazine, 2-amino-5-mercapto-1,3,4-thiadiazole, 2-methylamino-5-mercapto-1,3,4-thiadiazole, benzyl mercaptan, or dimercaptomethane. Thus there are employed for example, thiols of formula (III) where $R^2$ is alkyl, e.g. of 1 to 8 carbon atoms, mercapto lower alkyl, carboxyalkyl, e.g. having 2 to 3 carbon atoms in the alkyl group, lower alkyl carboxyalkyl, benzyl, phenyl, halophenyl, e.g. having 1 or 2 halogen atoms, e.g. chlorine, bromine or fluorine, lower alkyl phenyl, e.g. mono or di lower alkyl phenyl, lower alkoxyphenyl, e.g. mono or di lower alkoxy phenyl, trifluoromethylphenyl, cyanophenyl, nitrophenyl, lower alkyl mercaptophenyl, pyrimidyl, bis-(dilower alkylamino)-s-triazinyl, bis-(dilower alkoxy)-s-triazinyl, amino-1,3,4-thiadiazolyl, lower alkylamino-1,3,4-thiadiazolyl.

The addition of the thiol to the 2-chloroacrylic acid ester suitably is carried out in an inert solvent, such as an aliphatic or aromatic hydrocarbon e.g. cyclohexane, benzene, or toluene; an ether, e.g. dioxane, tetrahydrofuran, 1,2-dimethoxyethane, methyl-tert.butyl ether, diisopropyl ether or diethyl ether; a chlorinated hydrocarbon, e.g. methylene chloride, chloroform or 1,2-dichloroethane; or in special cases, also in water. However, the preferred solvent is methylene chloride. The reaction is carried out under the catalytic influence of the sodium or triethylammonium thiolate of the thiol employed, which thiolate advantageously can be formed in situ from the thiol and sodium or triethylamine. The sodium or triethylammonium thiolate is suitably added in an amount of 0.1 to 50 mole percent, preferably from 1 to 25 mole percent. The suitable temperature range for the reaction is between −40° and +80° C., especially between 0° and 30° C.

It is especially advantageous if there is present the 2-chloroacrylic acid ester together with at least a small part of the thiolate serving as catalyst in an inert solvent and the thiol, which in a given case contains the residual thiolate, slowly is added at room temperature, for example, in the course of 10 minutes up to one hour, and subsequently the mixture is stirred for a still longer time, for example, 10 minutes to 13 hours.

After the end of the reaction the solvent is drawn off under reduced pressure. The residue is taken up in diethyl ether and the undissolved thiolate remaining filtered off. After removal of the ether, at the end suitably in a high vacuum, there remains the S-substituted 2-chloro-3-mercapto-propionic acid ester formed as a yellow colored oil.

In the second reaction step subsequently the chloro atom of the S-substituted 2-chloro-3-mercapto-propionic acid ester of the general formula IV is exchanged with an azido group by means of an alkali metal azide. Preferably the exchange is carried out by means of sodium azide. The carrying out of the reaction suitably depends on the viscosity of the reacting S-substituted 2-chloro-3-mercapto-propionic acid ester. If this is of a relatively low viscosity the reaction is advantageously carried out in water, on the contrary if it is a relatively high viscosity oil, then it is better to carry out the reaction in acetonitrile. Since the reaction is suitably carried out at relatively low temperatures in the range between room temperature and 100° C., for example at about 40° to 60° C., to avoid undesired side reactions, the presence of a phase transfer catalyst is necessary. There are suitable all of the phase transfer catalysts known in the literature, such as quaternary ammonium and phosphonium salts or crown ethers. Preferably there are used quaternary ammonium salts, especially a commercial tri-($C_8$ to $C_{10}$-alkyl)methyl ammonium chloride ("Tricaprylylmethylammonium chloride", Aliquat 336). The phase transfer catalyst is suitably used in an amount between 0.5 and 20 mole percent, preferably between 1.0 and 5 mole percent, based on the S-substituted 2-chloro-3-mercapto-propionic acid ester employed. The alkali metal azide is suitably employed in excess, for example in 1.1 to 1.5 times the theoretically required amount. The exchange of the chlorine atom with the azido group generally requires a reaction time of 7 to 12 hours. For the production of the most complete reaction possible it is important to see to it that there is good intermixing of the heterogeneous system. The isolation of the S-substituted 2-azido-3-mercapto-propionic acid ester formed having the general formula (I) is advantageously carried out in such manner that the crude reaction mixture is extracted several times with diethyl ether, the combined extracts dried, for example with magnesium sulfate, and a chromatographic separation undertaken in a silica gel column. As mobile phase for the separation diethyl ether is especially suited.

In this chromatographic separation surprisingly impurities or by products are retained in the silica gel column so that the eluate after evaporation, suitably at reduced pressure, yields a colorless oil which according to its elemental analytical and spectroscopic data consists of the pure S-substituted 2-azido-3-mercapto-propionic acid ester of the general formula (I).

Then through the reduction of the azido group there can be produced from these new compounds the corresponding S-substituted D,L-cysteine esters. Since it is a matter of sulfur containing compounds the customary catalytic processes used for the reduction of azido groups are not suitable because the catalysts are very quickly poisoned.

The compounds of the general formula (I), however, can be reduced with hydrogen sulfide in a mixture of equal parts by volume of pyridine and water at room temperature within short reaction times of, for example, 2 hours to form the corresponding S-substituted D,L-cysteine esters.

It is more advantageous to undertake the reduction of the S-substituted 2-azido-3-mercapto-propionic acid ester by means of hydrogen in the presence of rhenium (VII) sulfide. The hydrogenation can be carried out in the temperature range between 20° and 100° C. without excess pressure or at hydrogen pressures up to 100 bar. Suitable solvents for the hydrogenation reaction are aqueous hydrochloric acid having a concentration between 0.1N and 10N, solutions of gaseous hydrogen chloride in a lower alkanol, e.g. methanol, ethanol, or isopropanol, or acetic anhydride. Depending on the reaction conditions used there are obtained as reaction products the corresponding S-substituted D,L-cysteine ester hydrochlorides, the corresponding S-substituted D,L-cysteine hydrochlorides or the corresponding S-substituted N-acetyl-D,L-cysteines.

Then in a known manner the methyl or benzyl group can readily be split off from the S-methyl or S-benzyl-D,L-cysteine hydrochloride so that there is obtained D,L-cysteine in good yield.

The processes can comprise, consist essentially of, or consist of the stated steps with the recited materials.

Unless otherwise indicated all parts and percentages are by weight.

The invention is explained in more detail through the following examples.

DETAILED DESCRIPTION

Example 1

There was added 0.219 gram (1.66 mmole) of sodium thiophenolate to 40.4 grams (335 mmoles) of freshly distilled 2-chloroacrylic acid methyl ester dissolved in 60 ml of water free methylene chloride. To this mixture there were added within 1 hour at 25° C. 1,97 grams (14.9 mmoles) of sodium thiophenolate and 36.6 grams (332 mmoles) of thiophenol portionwise and under stirring.

Stirring was continued for 4 hours at 25° C. and the solvent removed under reduced pressure. The residue was treated with 150 ml of diethyl ether, the precipitated sodium thiophenolate filtered off and the ether removed on the rotary evaporator under reduced pressure. There were obtained 70.0 grams (91% of theory) of 2-chloro-3-phenyl-mercaptan-propionic acid methyl ester as a yellowish oil.

| $C_{10}H_{11}ClO_2S$ (230.7) | C | H | S | Cl |
|---|---|---|---|---|
| Calculated: | 52.05% | 4.80% | 13.89% | 15.36% |
| Found: | 51.79% | 4.90% | 13.68% | 15.37% |

$^1$H-NMR(CDCl$_3$): δ=4,26(dd,1H)

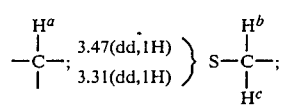

($J_{ab}$=9.93; $J_{ac}$=5.19; $J_{bc}$=−13.98 Hz) 3.76 (s,3H) COOC$\underline{H}_3$; 7.21–7.55 ppm (m,5H) C$_6$$\underline{H}_5$—.

Example 2

15.0 grams (65 mmoles) of the 2-chloro-3-phenylmercapto-propionic acid methyl ester produced in Example 1 was stirred together with 6.34 grams (97.5 mmoles) of sodium azide and 1.5 grams of the phase transfer catalyst Aliquat 336 in 30 ml of water for 8 hours at 50° C. After extraction of the aqueous phase with diethyl ether the organic phase was dried with magnesium sulfate, evaporated under reduced pressure and the residue filtered over a 10 cm silica gel column with diethyl ether as the mobile phase. After evaporation of the eluate under reduced pressure and removal of the residue of solvent in a high vacuum there remained 15.1 grams (98% of theory) of analytically pure 2-azido-3-phenylmercapto-propionic acid methyl ester.

| $C_{10}H_{11}N_3O_2S$ (237.2) | | | | |
|---|---|---|---|---|
| | C | H | N | S |
| Calculated: | 50.62% | 4.67% | 17.71% | 13.51% |
| Found: | 50.90% | 4.81% | 17.45% | 13.72% |

$^1$H-NMR(CDCl$_3$): δ=3.99(dd,1H)

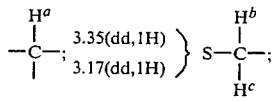

($J_{ab}$=5.67; $J_{ac}$=7.67; $J_{bc}$=−14.04 Hz)
3.69(s,3H)—COOC$\underline{H}_3$; 7.18–7.75 ppm (m,5H) C$_6\underline{H}_5$—.

Example 3

There was added 0.143 gram (0.98 mmole) of sodium benzylthiolate to 23.5 grams (195 mmoles) of freshly distilled 2-chloroacrylic acid methyl ester dissolved in 40 ml of water free methylene chloride. To this mixture there were fed in within 1 hour at 25° C. 1.29 grams (8.82 mmoles) of sodium benzylthiolate and 24.22 grams (195 mmoles) of benzyl mercaptan.

Stirring was continued for 4 hours at 25° C. The working up according to Example 1 gave 45.4 grams (95% of theory) of 2-chloro-3-benzylmercapto-propionic acid methyl ester as a yellowish oil.

| $C_{11}H_{13}ClO_2S$ (244.8) | | | | |
|---|---|---|---|---|
| | C | H | S | Cl |
| Calculated: | 53.98% | 5.35% | 14.48% | 13.10% |
| Found: | 54.16% | 5.50% | 14.34% | 13.25% |

$^1$H-NMR(CDCl$_3$): δ=4.19(dd,1H)

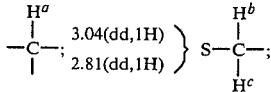

($J_{ab}$=9.66; $J_{ac}$=5.40; $J_{bc}$=−14.09 Hz)
3.76(s,3H)—COOC$\underline{H}_3$; 7.29($\overline{s}$,5H)—C$_6\underline{H}_5$; 3.73 ppm (s,2H) C$_6$H$_5$—C$\underline{H}_2$—.

Example 4

15.0 grams (61.3 mmoles) of the 2-chloro-3-benzylmercapto-propionic acid methyl ester produced in Example 3 were stirred with 5.98 grams (92.0 mmoles) of sodium azide and 1.5 grams of Aliquat 336 in 30 ml of water for 7 hours at 45° C. After working up according to Example 2 there were obtained 15.2 grams (99% of theory) of 2-azido-3-benzylmercapto-propionic acid methyl ester.

| $C_{11}H_{13}N_3O_2S$ (251.3) | | | | |
|---|---|---|---|---|
| | C | H | N | S |
| Calculated: | 52.57% | 5.21% | 16.72% | 12.76% |
| Found: | 52.79% | 5.21% | 15.09% | 12.47% |

$^1$H-NMR(CDCl$_3$): δ=3.95(dd,1H)

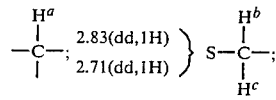

($J_{ab}$=5.24; $J_{ac}$=7.56; $J_{bc}$=−14.04 Hz)
3.76(s,3H)—COOC$\underline{H}_3$; 7.30($\overline{s}$,5H)—C$_6\underline{H}_5$; 3.77 ppm (s,2H) C$_6$H$_5$—C$\underline{H}_2$—.

Example 5

12.05 grams (100 mmoles) of freshly distilled 2-chloroacrylic acid methyl ester (methyl-2-chloroacrylate) were dissolved in 30 ml of water free methylene chloride and treated with 0.035 gram (0.5 mmole) of sodium methylthiolate. There were then dosed into the mixture within 1 hour at 25° C. 0.315 grams (4.5 mmoles) of sodium methylthiolate and there were led in 9.62 grams (200 mmoles) of methyl mercaptan. Post stirring was subsequently employed for a further 4 hours at the stated temperature.

After working up according to Example 1 there were obtained 14.6 grams (86% of theory) of 2-chloro-3-methylmercapto-propionic acid methyl ester as a yellowish oil.

| $C_5H_9ClO_2S$ (168.8) | | | | |
|---|---|---|---|---|
| | C | H | S | Cl |
| Calculated: | 35.61% | 5.38% | 21.02% | 19.01% |
| Found: | 35.88% | 5.52% | 21.01% | 19.14% |

$^1$H-NMR(CDCl$_3$): δ=4.38(dd,1H)

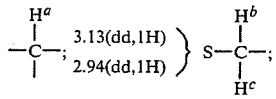

($J_{ab}$=9.68; $J_{ac}$=5.32; $J_{bc}$=−13.98 Hz)
3.82(s,3H)—COOC$\underline{H}_3$; 2.17 ppm (s,3H)—S—C$\underline{H}_3$.

Example 6

6.0 grams (35.5 mmoles) of the 2-chloro-3-methylmercapto-propionic acid methyl ester produced in Example 5 were stirred with 3.47 grams (53.4 mmoles) of sodium azide and 0.82 grams of Aliquat 336 in 15 ml of water for 7 hours at 45° C. After working up according to Example 2 there were obtained 5.44 grams (87% of theory) of 2-azido-3-methylmercapto-propionic acid methyl ester as an analytically pure material.

| $C_5H_9N_3O_2S$ (175.2) | | | | |
|---|---|---|---|---|
| | C | H | N | S |
| Calculated: | 34.28% | 5.18% | 23.98% | 18.30% |
| Found: | 34.26% | 5.22% | 23.72% | 18.54% |

$^1$H-NMR(CDCl$_3$): δ=4.11(dd,1H)

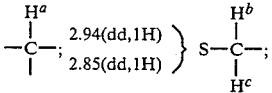

($J_{ab}$=5.63; $J_{ac}$=7.40; $J_{bc}$=−14.02 Hz)
3.82(s,3H)—COOCH$_3$; 2.19 ppm (s,3H)—S—C$\underline{H}_3$.

Example 7

0.076 gram (3.31 mmoles) of metallic sodium were dissolved in 17.97 grams (169 mmoles) of thioglycolic acid methyl ester. This solution was then subsequently under stirring dropped into 20.0 grams (166 mmoles) of freshly distilled 2-chloro-acrylic acid methyl ester dissolved in 30 ml of water free methylene chloride within 1 hour at 25° C. After 4 hours post reaction at 25° C. it was worked up according to Example 1. There were obtained 37.5 grams (99.6% of theory) of 2-chloro-3-methoxycarbonylmethylmercapto-propionic acid methyl ester as a yellowish oil.

| $C_7H_{11}ClO_4S$ (226.7) | C | H | S | Cl |
|---|---|---|---|---|
| Calculated: | 37.09% | 4.89% | 14.15% | 15.64% |
| Found: | 37.03% | 4.71% | 14.08% | 15.90% |

$^1$H-NMR(CDCl$_3$): δ=4.47(dd,1H)

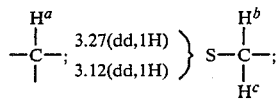

($J_{ab}$=9.26; $J_{ac}$=5.64; $J_{bc}$=−14.19 Hz) 3.83(s,3H)—COOC$\underline{H}_3$; 3.76(s,3H)—COOC$\underline{H}_3$; 3.31 ppm (s,2H)—S—C$\underline{H}_2$—COOCH$_3$.

Example 8

15.0 grams (66.2 mmoles) of the 2-chloro-3-methoxycarbonylmethylmercapto-propionic acid methyl ester produced in Example 7 were stirred with 6.45 grams (99.2 mmoles) of sodium azide and 0.75 gram of Aliquat 336 in 30 ml of water for 8 hours at 50° C. and subsequently stirred for 63 hours at 25° C.

After working up according to Example 2 there were obtained 15.0 grams (97% of theory) of 2-azido-3-methoxycarbonylmethylmercapto-propionic acid methyl ester as an analytically pure compound.

| $C_7H_{11}N_3O_4S$ (233.3) | C | H | N | S |
|---|---|---|---|---|
| Calculated: | 36.05% | 4.75% | 18.02% | 13.75% |
| Found: | 36.31% | 4.83% | 18.06% | 13.58% |

$^1$H-NMR(CDCl$_3$): δ=4.23(dd,1H)

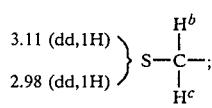

($J_{ab}$=5.27: $J_{ac}$=7.65; $J_{bc}$=−14.18 Hz) 3.83(s,3H)—COOC$\underline{H}_3$; 3.76(s,3H)—COOC$\underline{H}_3$; 3.35 ppm (s,2H)—S—C$\underline{H}_2$—COOCH$_3$.

Example 9

Under stirring there were added 0.063 gram (1.58 mmoles) of sodium hydroxide in 0.32 ml water to 1.00 gram (10.9 mmoles) of mercaptoacetic acid and 1.31 grams (10.9 mmoles) of 2-chloroacrylic acid methyl ester. Stirring was carried out subsequently for 24 hours at 10° C. After acidification of the reaction mixture with dilute hydrochloric acid the working up was carried out by extracting three times with diethyl ether, drying the combined ether phases with water free sodium sulfate and removal of the ether. There were obtained 2.00 grams (86% of theory) of 2-chloro-3-carboxymethylmercapto-propionic acid methyl ester as a colorless viscous oil.

| $C_6H_9ClO_4S$ (212.7) | C | H | S | Cl |
|---|---|---|---|---|
| Calculated: | 33.89% | 4.27% | 15.08% | 16.67% |
| Found: | 33.66% | 4.28% | 15.02% | 16.40% |

$^1$H-NMR(CDCl$_3$): δ=4.48(dd,1H)

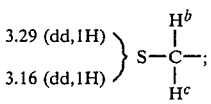

($J_{ab}$=9.11; $J_{ac}$=5.66; $J_{bc}$=14.26 Hz) 3.83(s,3H)—COOC$\underline{H}_3$; 3.35(s,2H)—S—C$\underline{H}_2$COOH; 9.84 ppm (s,1H)—COO$\underline{H}$—.

Example 10

1.00 gram (4.70 mmoles) of the 2-chloro-3-carboxymethylmercapto-propionic acid methyl ester produced in Example 9 was stirred with 0.46 gram (7.08 mmoles) of sodium azide and 0.10 gram of Aliquat 336 in 2 ml of water for 15 hours at 50° C. After working up according to Example 2 there were obtained 0.91 gram (88% of theory) of 2-azido-3-carboxymethylmercapto-propionic acid methyl ester as an analytically pure material.

| $C_6H_9N_3O_4S$ (219.2) | C | H | N | S |
|---|---|---|---|---|
| Calculated: | 32.87% | 4.14% | 19.17% | 14.63% |
| Found: | 32.87% | 4.01% | 18.91% | 14.68% |

$^1$H-NMR(CDCl$_3$): δ=4.28(dd,1H)

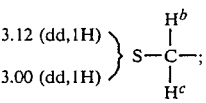

($J_{ab}$=5.12; $J_{ac}$=7.56; $J_{bc}$=−14.26 Hz) 3.84(s,3H)—COOC$\underline{H}_3$; 3.40(s,2H)—S—C$\underline{H}_2$—COOH; 10.01 ppm (s,1H)—S—CH$_2$—COO$\underline{H}$.

Example 11

At 25° C. there were added 0.252 gram (2.49 mmoles) of triethylamine and 2.76 grams (24.6 mmoles) of 2-mercapto-pyrimidine were added to 3.0 grams (24.9 mmoles) of freshly distilled 2-chloroacrylic acid methyl ester dissolved in 15 ml of water free methylene chloride. Stirring was carried out for 1.5 hours and then the solvent and triethylamine removed under reduced pressure. To remove the last traces of the triethylamine the product in methylene chloride was filtered over a short silica gel column. Concentration of the filtrate then yielded 5.3 grams (92% of theory) of 2-chloro-3-(2'-pyrimidylmercapto)-propionic acid methyl ester as a yellowish viscous oil.

| $C_8H_9ClN_2O_2S$ (232.7) | C | H | N | S | Cl |
|---|---|---|---|---|---|
| Calculated: | 41.30% | 3.90% | 12.04% | 13.78% | 15.24% |
| Found: | 41.11% | 3.81% | 11.99% | 14.04% | 15.08% |

$^1$H-NMR(CDCl$_3$): δ=4.65(dd,1H)

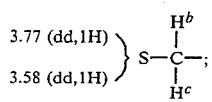

($J_{ab}$=5.59; $J_{ac}$=9.40; $J_{bc}$=−13.91 Hz) 3.81(s,3H)—COOC$\underline{H}_3$; 8.55(d,2H)

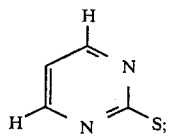

7.06(t,1H)

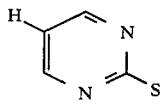

(J=4.94 Hz).

Example 12

3.84 grams (16.5 mmoles) of 2-chloro-3-(2'-pyrimidylmercapto)-propionic acid methyl ester produced according to Example 11 were stirred together with 1.62 grams (24.9 mmoles) of sodium azide and 0.7 gram of Aliquat 336 in 5 ml of acetonitrile for 12 hours at 40° C.

After the end of the reaction the acetonitrile was drawn off under reduced pressure on the rotary evaporator, the residue was taken up in diethyl ether, filtered, the filtrate concentrated and the residue chromatographed and worked up according to Example 2. There were obtained 3.36 grams (85% of theory) of 2-azido-3-(2'-pyrimidylmercapto)-propionic acid methyl ester as an analytically pure material.

| $C_8H_9N_5O_2S$ (239.3) | C | H | N | S |
|---|---|---|---|---|
| Calculated: | 40.16% | 3.79% | 29.27% | 13.40% |
| Found: | 40.42% | 3.74% | 29.34% | 13.60% |

$^1$H-NMR(CDCl$_3$): δ=4.35(dd,1H)

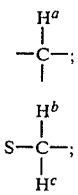

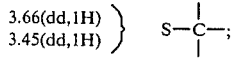

($J_{ab}$=6.14; $J_{ac}$=7.68; $J_{bc}$=−14.09 Hz) 3.82(s,3H)—COOC$\underline{H}_3$; 8.54(d,2H)

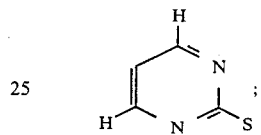

7.04 ppm (t,1H)

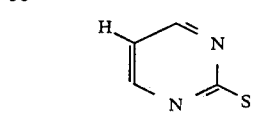

(J=4.80 Hz).

Example 13

There were added 0.365 grams (3.61 mmoles) of triethylamine in 5 ml of diethyl ether at 0° C. within 20 minutes to 4.51 grams (56.3 mmoles) of dimercaptomethane and 20.4 grams (169 mmoles) of freshly distilled 2-chloroacrylic acid methyl ester in 20 ml of diethyl ether. After a further 10 minutes there were added 20 ml of aqueous sodium acetate solution, the organic phase separated off and washed twice with 20 ml of water. After drying the organic phase over sodium sulfate the solvent was removed under reduced pressure. There were obtained 13.5 grams (75% of theory) of the mixture of diastereomers of 2-chloro-3-(2'-chloro-2'-methoxycarbonylethylmercaptomethylmercapto)-propionic acid methyl ester as a colorless oil.

| $C_9H_{14}Cl_2S_2O_4$ (321.2) | C | H | S | Cl |
|---|---|---|---|---|
| Calculated: | 33.65% | 4.39% | 19.96% | 22.07% |
| Found: | 33.73% | 4.14% | 20.04% | 22.01% |

$^1$H-NMR(CDCl$_3$): δ=4.45(dd,1H); 4.53(dd,1H) (Diastereomers)

3.34 (dd,1H); 3.32 (dd,1H)  
3.16 (dd,1H); 3.16 (dd,1H) 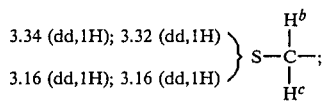

($J_{ab}$=8.84 Hz; $J_{ab}$=8.85 Hz; $J_{ac}$=5.78 Hz; $J_{ac}$=5.78 Hz; $J_{bc}$=−14.01 Hz; $J_{bc}$=−13.97 Hz) 3.83(s,6H)—COOC$\underline{H_3}$; 3.78 ppm (s,2H)—S—C$\underline{H_2}$—S—.

Example 14

7.0 grams (21.8 mmoles) of the 2-chloro-3-(2'-chloro-2'-methoxycarbonylethylmercaptomethylmercapto)-propionic acid methyl ester produced according to Example 13 were stirred with 4.25 grams (65.4 mmoles) of sodium azide and 0.5 grams of Aliquat 336 in 12 ml of water for 12 hours at 55° C. After working up according to Example 2 there were obtained 6.52 grams (89% of theory) of 2-azido-3-(2'-azido-2'-methoxycarbonylethylmercaptomethylmercapto)-propionic acid methyl ester as an analytically pure material.

| $C_9H_{14}N_6O_4S_2$ (334.4) | C | H | N | S |
|---|---|---|---|---|
| Calculated: | 32.23% | 4.27% | 25.13% | 19.18% |
| Found: | 32.12% | 4.21% | 25.40% | 19.28% |

$^1$H-NMR(CDCl$_3$): δ=4.23(dd,1H)

3.10 (dd,1H)  
2.98 (dd,1H) 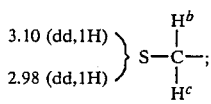

($J_{ab}$=5.29; $J_{ac}$=7.49; $J_{bc}$=−14.15 Hz) 3.83(s,6H)—COOC$\underline{H_3}$; 3.85 ppm (s,2H)—S—C$\underline{H_2}$—S—.

Example 15

There was led into 6.3 grams (26.6 mmoles) of the 2-azido-3-phenylmercapto-propionic acid methylester produced according to Example 2 in 80 ml of a 50 volume percent aqueous pyridine solution under stirring at 25° C. a weak stream of hydrogen sulfide. After this time the development of gas was ended. The reaction mixture was freed from the pyridine portion on a rotary evaporator under reduced pressure and the aqueous solution remaining behind extracted 3 times, each time with 40 ml of diethyl ether. The combined organic extracts were dried over magnesium sulfate, the ether removed on a rotary evaporator and the residue freed from residual solvent in a high vacuum. Chromatography on a silica gel column with ethyl acetate yielded 5.06 grams (90% of theory) of S-phenyl cysteine methyl ester.

| $C_{10}H_{13}NO_2S$ (211.3) | C | H | N | S |
|---|---|---|---|---|
| Calculated: | 56.85% | 6.20% | 6.63% | 15.18% |
| Found: | 56.92% | 6.13% | 6.45% | 15.15% |

$^1$H-NMR(CDCl$_3$): δ=3.65(dd,1H)

3.34(dd,1H)  
3.14(dd,1H) 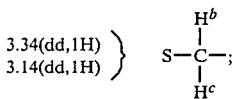

($J_{ab}$=4.68; $J_{ac}$=7.25; $J_{bc}$=−13.65 Hz) 1.88(s,2H)—N$\underline{H_2}$; 3.57(s,3H)—COOC$\underline{H_3}$; 7.08–7.46 ppm (m,5H)—C$_6\underline{H_5}$.

Example 16

A weak stream of hydrogen sulfide was led into 6.3 grams (25.1 mmoles) of the 2-azido-3-benzylmercapto-propionic acid methyl ester produced in Example 4 in 80 ml of a 50 volume percent aqueous pyridine solution for 2 hours at 25° C.

After working up according to Example 15 there were obtained 4.54 grams (80% of theory) of S-benzyl-cysteine methyl ester.

| $C_{11}H_{15}NO_2S$ (225.3) | C | H | N | S |
|---|---|---|---|---|
| Calculated: | 58.64% | 6.71% | 6.22% | 14.23% |
| Found: | 58.60% | 6.64% | 6.14% | 13.94% |

$^1$H-NMR(CDCl$_3$): δ=3.60(dd,1H)

2.83(dd,1H)  
2.67(dd,1H) 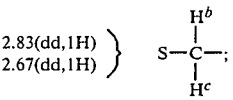

($J_{ab}$=4.73; $J_{ac}$=7.49; $J_{bc}$=−13.56 Hz) 1.89(s,2H)—N$\underline{H_2}$; 3.73(s,3H)—COOC$\underline{H_3}$; 7.30(s,5H)—C$_6\underline{H_5}$; 3.71 ppm (s,2H) C$_6$H$_5$—C$\underline{H_2}$—.

Example 17

Hydrogen sulfide was led into 4.16 grams (23.7 mmoles) of the 2-azido-3-methylmercapto-propionic acid methyl ester produced in Example 6 in 60 ml of a 50 volume percent aqueous pyridine solution.

After working up according to Example 15 there were obtained 2.06 grams (58% of theory) of S-methyl-cysteine methyl ester.

$^1$H-NMR(CDCl$_3$): δ=3.68(dd,1H)

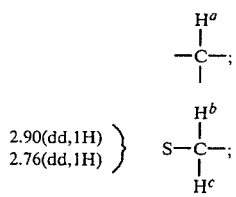

$(J_{ab}=4.78; \quad J_{ac}=7.31; \quad J_{bc}=-13.62 \quad Hz)$
1.99(s,2H)—N$\underline{H_2}$; 3.75(s,3H)—COOC$\underline{H_3}$; 2.13 ppm (s,3H)—S—C$\underline{H_3}$.

Example 18

A weak stream of hydrogen sulfide was led into 1.0 gram (4.18 mmoles) of the 2-azido-3-(2'-pyrimidylmercapto)-propionic acid methyl ester produced in Example 12 in 5 ml of a 40 volume percent aqueous pyridine solution for 2 hours at 25° C.

The working up according to Example 15 resulted in 0.65 gram (73% of theory) of S-(2'-pyrimidyl)-cysteine methyl ester as a yellow viscous product.

$C_8H_{11}N_3O_2S$ (213.3): Highly Dissolved Masspectrum: Calculated: 213.0572. Found: 213.0573.

$^1$H-NMR(CDCl$_3$): $\delta = 4.34$(dd,1H)

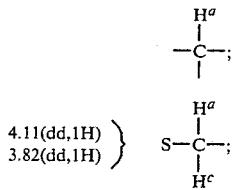

$(J_{ab}=5.15; \quad J_{ac}=7.43; \quad J_{bc}=-13.84 \quad Hz)$
2.17(s,2H)—N$\underline{H_2}$; 3.75(s,3H)—COOC$\underline{H_3}$; 8.53(d,2H)

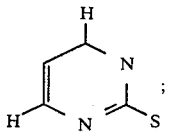

7.01 ppm (t,1H)

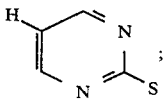

(J=4.90 Hz).

EXAMPLE 19

0.91 gram (3.84 mmoles) of the 2-azido-3-phenylmercapto-propionic acid methyl ester obtained in Example 2 in 8 ml of methanol was treated with 0.28 gram (7.68 mmoles) of hydrogen chloride, 1 mole % of rhenium VII sulfide based on the azido compound employed was added and the mixture hydrogenated in an autoclave at a hydrogen pressure of 60 bar at 25° C. for 3.5 hours. After the end of the reaction the catalyst was filtered off with suction, the solvent remained under reduced pressure and the residue treated with 20 ml of acetone. After addition of 20 ml of diethyl ether for complete precipitation, the precipitate was filtered off with suction, then washed with diethyl ether and dried at 40° C. for 12 hours under reduced pressure. There were obtained 0.65 gram (68% of theory) of 2-amino-3-phenylmercapto-propionic acid methyl ester.HCl with a melting point of 123° to 125° C.

EXAMPLE 20

1.00 gram (4.29 mmoles) of the 2-azido-3-methoxycarbonylmethylmercapto-propionic acid methyl ester obtained in Example 8 in 8 ml of methanol was reacted with 1 mole % of rhenium VII sulfide under addition of 0.32 gram (8.78 mmoles) of hydrogen chloride gas and hydrogenation in accordance with Example 19.

The working up gave 0.87 gram (83% of theory) of 2-amino-3-phenylmercapto-propionic acid methyl ester.HCl having a melting point of 104.5° to 105.5° C.

| $C_7H_{14}NO_4SCl$ (243.7) | | | | | |
|---|---|---|---|---|---|
| | C | H | N | S | Cl |
| Calculated: | 34.50% | 5.79% | 5.75% | 13.16% | 14.55% |
| Found: | 34.55% | 5.89% | 5.72% | 13.14% | 14.20% |

$^1$H-NMR(D$_2$O): $\delta = 4.44$(dd,1H)

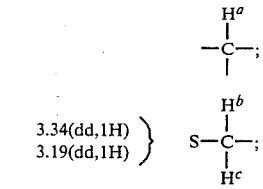

$(J_{ab}=4.66; \quad J_{ac}=7.89; \quad J_{bc}=-15.11 \quad Hz)$
3.87(s,3H)—COOC$\underline{H_3}$; 3.77(s,3H)—COOC$\underline{H_3}$; 3.53(s,2H)—S—C$\underline{H_2}$—COOCH$_3$; 4.78 ppm (s,H$_2$O).

EXAMPLE 21

0.91 gram (3.62 mmoles) of the 2-azido-3-benzylmercapto-propionic acid methyl ester obtained in Example 4 was dissolved in 8 ml of methanol, treated with 0.27 gram (7.41 mmoles) of HCl gas and there was added 1 mole % of rhenium VII sulfide, based on the amount of azido compound employed. Hydrogen was led into this vigorously stirred reaction mixture for 45 hours. The working up according to Example 19 gave 0.60 gram (63% of theory) of S-benzyl-cysteine methyl ester.HCl having a melting point of 84° to 87° C.

EXAMPLE 22

0.61 grams (3.48 mmoles) of the 2-azido-3-methylmercapto-propionic acid methyl ester obtained in Example 6 in 7 ml of methanol with 1 mole % of rhenium VII sulfide under addition of 0.25 gram (6.86 mmoles) of HCl gas were hydrogenated according to Example 21 but for only 42 hours.

After working up there were obtained 0.52 gram (80% of theory) of 2-amino-3-methylmercapto-propionic acid methyl ester.HCl having a melting point of 107° to 108° C.

| $C_5H_{12}NO_2SCl$ (185.67) | | | | | |
|---|---|---|---|---|---|
| | C | H | N | S | Cl |
| Calculated: | 32.84% | 6.51% | 7.54% | 17.27% | 19.09% |
| Found: | 30.57% | 6.52% | 8.14% | 16.57% | 20.82% |

EXAMPLE 23

0.91 gram (3.84 mmoles) of the 2-azido-2-phenylmercapto-propionic acid methyl ester obtained in Example 2 was hydrogenated in 10 ml of 3N hydrochloric acid in the presence of 1 mole % of rhenium VII sulfide, based on the azido compound employed in an autoclave at 110° C. and 50 bar of hydrogen pressure up to complete reaction.

After the end of the reaction the catalyst was filtered off, the reaction mixture evaporated to dryness and the residue taken up in the least possible amount of water. After treating this clear solution with acetone the precipitate was filtered off with suction and dried at 40° C. for 24 hours at reduced pressure. There were obtained 0.70 grams (78% of theory) of S-phenylcysteine.HCl having a melting point of 203° to 204° C. (decomposition).

Neutralization of the aqueous solution of this solid material with ammonia after filtering with suction gave 0.57 gram (75% of theory) of S-phenylcysteine having a melting point of 187° to 188° C. (decomposition). Literature: 190° C. (decomposition)).

| $C_9H_{11}NO_2S$ (197.3) | | | | |
|---|---|---|---|---|
| | C | H | N | S |
| Calculated: | 54.80% | 5.62% | 7.10% | 16.26% |
| Found: | 54.36% | 5.42% | 6.83% | 16.13% |

$^1$H-NMR(NaOD/D$_2$O): $\delta$ = 2.90 bis 3.48 (m,3H)

—S—C$\underline{H_2}$—C$\underline{H}$—;

5.07(s,H$_2$O); 7.65 bis 7.31 ppm (m,5H)—C$_6$H$_5$.

EXAMPLE 24

0.91 gram (3.62 mmoles) of the 2-azido-3-benzylmercapto-propionic acid methyl ester obtained in Example 4 was reacted according to Example 23.

After working up there were obtained 0.68 gram (76% of theory) of S-benzyl-cysteine.HCl having a melting point of 206° C. (decomposition).

Neutralization of the aqueous solution with ammonia yielded 0.50 gram (65% of theory of 1 of S-benzyl-cysteine having a melting point of 217° to 218° C. (decomposition). Literature: 215° to 216° C. (decomposition)).

| $C_{10}H_{13}NO_2S$ (211.3) | | | | |
|---|---|---|---|---|
| | C | H | N | S |
| Calculated: | 56.85% | 6.20% | 6.63% | 15.18% |
| Found: | 57.06% | 6.14% | 6.66% | 15.00% |

$^1$H-NMR(NaOD/D$_2$O): $\delta$ = 3.38(dd,1H)

$$\begin{array}{c} H^a \\ | \\ -C- \\ | \end{array} ;$$

$$\left. \begin{array}{l} 2.78 \text{ (dd, 1H)} \\ 2.68 \text{ (dd, 1H)} \end{array} \right\} \; S-\underset{\underset{H^c}{|}}{\overset{\overset{H^b}{|}}{C}}- ;$$

($J_{ab}$=5.00; $J_{ac}$=7.02; $J_{bc}$=−13.49 Hz) 4.88(s,H$_2$O) 7.37(s,5H)—C$_6$H$_5$; 3.75 ppm (s,2H) C$_6$H$_5$—C$\underline{H_2}$—.

EXAMPLE 25

0.70 gram (4.00 mmoles) of the 2-azido-3-methylmercapto-propionic acid methyl ester obtained in Example 6 were reacted according to Example 23.

After removing the catalyst with suction the solution was concentrated to dryness under reduced pressure. Then it was taken up with a little water, neutralized with dilute ammonia solution and the free amino acid precipitated with ethanol. There were obtained in this manner 0.28 gram (52% of theory) of S-methyl-cysteine having a melting point of 215° to 217° C. (decomposition). (Literature: 240° C. (decomposition)).

| $C_4H_9NO_2S$ (135.2) | | | | |
|---|---|---|---|---|
| | C | H | N | S |
| Calculated: | 35.54% | 6.71% | 10.36% | 23.72% |
| Found: | 35.36% | 6.74% | 10.27% | 23.98% |

$^1$H-NMR(NaOD/D$_2$O): $\delta$ = 3.44(dd,1H)

$$\begin{array}{c} H^a \\ | \\ -C- \\ | \end{array} ;$$

$$\left. \begin{array}{l} 2.84 \text{ (dd, 1H)} \\ 2.75 \text{ (dd, 1H)} \end{array} \right\} \; S-\underset{\underset{H^c}{|}}{\overset{\overset{H^b}{|}}{C}}- ;$$

($J_{ab}$=5.00; $J_{ac}$=7.06; $J_{bc}$=−13.57 Hz) 4.86 ppm (s,H$_2$O).

EXAMPLE 26

1.00 gram (4.29 mmoles) of the 2-azido-3-methoxycarbonylmethylmercapto-propionic acid methyl ester obtained in Example 8 was reacted according to Example 23.

After filtering off the catalyst with suction the product was concentrated to dryness under reduced pressure. After addition of a little water, it was adjusted to a pH of 3 to 4 with dilute potassium hydroxide. After filtering with suction and drying, there was obtained 0.47 gram (61% of theory) of DL-S-carboxymethyl-cysteine having a melting point of 188° to 191° C. (decomposition).

| $C_5H_9NO_4S$ (179.2) | | | | |
|---|---|---|---|---|
| | C | H | N | S |
| | 33.51% | 5.06% | 7.82% | 17.89% |
| | 33.27% | 5.17% | 7.57% | 17.98% |

$^1$H-NMR(DCl/D$_2$O): $\delta$ = 4.38(dd,1H)

$$\begin{array}{c} H^a \\ | \\ -C- \\ | \end{array} ;$$

$$\begin{matrix} 3.34 \text{ (dd, 1H)} \\ 3.20 \text{ (dd, 1H)} \end{matrix} \Bigg\} \text{S}-\underset{\underset{H^c}{|}}{\overset{\overset{H^b}{|}}{C}}-;$$

($J_{ab}$=4.33; $J_{ac}$=7.95; $J_{bc}$=−15.15 Hz)
3.53(s,2H)—S—C$\underline{H_2}$—COOH; 4.95 ppm (s,H$_2$O).

EXAMPLE 27

1.00 gram (2.99 mmoles) of the 2-azido-3-(2'-azido-2'-methoxycarbonylethylmercaptomethylmercapto)-propionic acid methyl ester obtained in Example 14 was reacted according to Example 23.

After filtering off the catalyst with suction, the product was concentrated to dryness, the residue taken up in water, brought to pH 4 to 5 with aqueous sodium hydroxide and a pH of 5 to 6 established with an aqueous sodium acetate. After filtering off the product with suction and drying there were obtained 0.43 gram (57% of theory) of methylene-bis-cysteine having a melting point of 239°–241° C. (decomposition).

| C$_7$H$_{14}$N$_2$O$_4$S$_2$ (254.3) | | | | |
|---|---|---|---|---|
| | C | H | N | S |
| Calculated: | 33.06% | 5.55% | 11.01% | 25.22% |
| Found: | 32.56% | 5.12% | 11.36% | 24.50% |

$^1$H-NMR(DCl/D$_2$O): δ=4.33(dd,1H)

$$-\underset{|}{\overset{\overset{H^a}{|}}{C}}-;$$

$$\begin{matrix} 3.39 \text{ (dd, 1H)} \\ 3.25 \text{ (dd, 1H)} \end{matrix} \Bigg\} \text{S}-\underset{\underset{H^c}{|}}{\overset{\overset{H^b}{|}}{C}}-;$$

($J_{ab}$=4.39; $J_{ac}$=7.44; $J_{bc}$=−14.98 Hz)
3.90(s,2H)—S—C$\underline{H_2}$—S—; 4.80 ppm (s,H$_2$O).

EXAMPLE 28

1.00 gram (4.22 mmoles) of the 2-azido-3-phenylmercapto-propionic acid methyl ester obtained in Example 2 was dissolved in 5 ml of acetic anhydride and then was added 1 mole % of rhenium VII sulfide based on the azido compound employed. Under vigorous stirring there was led hydrogen through the solution for 24 hours at 70° C. After the end of the reaction the solvent was drawn off under reduced pressure on the rotary evaporator, the product taken up in diethyl ether and the catalyst filtered off. Chromatography on a silica gel column with petroleum ether/ethyl acetate (volume ratio 1:1) gave 0.50 gram (47% of theory) of N-acetyl-S-phenyl-cysteine methyl ester as a colorless oil.

| C$_{12}$H$_{15}$NO$_3$S (253.3) | | | | |
|---|---|---|---|---|
| | C | H | N | S |
| Calculated: | 56.90% | 5.97% | 5.53% | 12.66% |
| Found: | 56.00% | 5.67% | 5.76% | 12.59% |

$^1$H-NMR(CDCl$_3$): δ=4.85(dd,1H)

$$-\underset{|}{\overset{\overset{H^a}{|}}{C}}-;$$

$$\begin{matrix} 3.47 \text{ (dd, 1H)} \\ 3.35 \text{ (dd, 1H)} \end{matrix} \Bigg\} \text{S}-\underset{\underset{H^c}{|}}{\overset{\overset{H^b}{|}}{C}}-;$$

($J_{ab}$=4.72; $J_{ac}$=4.71; $J_{bc}$=−14.19 Hz) 7.16–7.59 (m,5H)—C$_6$$\underline{H_5}$; 3.56(s,3H)—COOC$\underline{H_3}$;

1.88 (s, 3H) —N—C—CH$_3$;
$\qquad\qquad\qquad$ | ‖
$\qquad\qquad\qquad$ $\quad$ O 6.44 ppm ($\bar{\text{d}}$, 1H)—N$\underline{H}^d$ ($J_{ad}$=7.5 Hz).

EXAMPLE 29

1.00 gram (4.29 mmoles) of the 2-azido-3-methoxycarbonylmethylmercapto-propionic acid methyl ester obtained in Example 8 were hydrogenated in a manner analogous to Example 28 for 15 hours.

After working up according to Example 28 there was obtained 0.39 gram (36% of theory) of S-methoxycarbonylmethyl-N-acetyl-cysteine methyl ester as a colorless oil.

| C$_9$H$_{15}$NO$_5$S (249.3) | | | | |
|---|---|---|---|---|
| | C | H | N | S |
| Calculated: | 43.36% | 6.07% | 5.62% | 12.86% |
| Found: | 43.30% | 5.99% | 5.44% | 13.10% |

$^1$H-NMR(CDCl$_3$): δ=4.86(dt,1H)

$$-\underset{|}{\overset{\overset{H^a}{|}}{C}}-;$$

3.09(d,2H) —S—C$\underline{H_2}^{b+}$—; ($J_{ab}$=5.57 Hz)
6.73($\bar{\text{d}}$,1H)—N$\underline{H}^c$—; ($J_{ac}$=7.74 Hz)
3.77(s,3H)—COOC$\underline{H_3}$; 3.75(s,3H)—COOC$\underline{H_3}$;

$$\begin{matrix} 3.30 \text{ (s, 1H)} \\ 3.29 \text{ (s, 1H)} \end{matrix} \Bigg\} -\text{S}-\text{C}\underline{H_2}-\text{COOCH}_3;$$

2.07 ppm (s, 3H) —N—C—CH$_3$.
$\qquad\qquad\qquad$ | ‖
$\qquad\qquad\qquad$ $\quad$ O

What is claimed is:
1. An S-substituted 2-azido-3-mercapto-propionic acid ester of the formula:

$$R^2-S-CH_2-\underset{\underset{N_3}{|}}{CH}-COOR^1 \qquad (I)$$

where R$^1$ is a methyl or ethyl group and R$^2$ is an alkyl group of 1 to 8 carbon atoms, a mercapto lower alkyl group, a carboxyalkyl group having 2 to 3 carbon atoms, a lower alkyl oxycarbonyl 1-2 carbon atom alkyl group, a cyclopentyl group, a cyclohexyl group, a phenyl group, a halophenyl group, a lower alkyl phenyl group, a pyrimidyl group, or a benzyl group.

2. An ester according to claim 1 wherein $R^2$ is alkyl of 1 to 8 carbon atoms, mercapto lower alkyl, carboxyalkyl having 2 to 3 carbon atoms, lower alkyl oxycarbonyl-1 to 2-carbon atom alkyl, cyclopentyl, cyclohexyl, phenyl, or lower alkyl phenyl.

3. An ester according to claim 1 where $R^2$ is phenyl.

4. An ester according to claim 1 where $R^2$ is benzyl.

5. An ester according to claim 1 where $R^2$ is alkyl of 1 to 8 carbon atoms.

6. An ester according to claim 5 where $R^2$ is methyl.

7. An ester according to claim 1 where $R^2$ is methoxycarbonylmethyl or methoxycarbonylethyl.

8. An ester according to claim 1 where $R^2$ is carboxymethyl.

9. An ester according to claim 1 where $R^2$ is pyrimidyl.

* * * * *